United States Patent
Hunt et al.

(10) Patent No.: US 7,547,881 B2
(45) Date of Patent: Jun. 16, 2009

(54) NANOWIRE ELECTRON SCATTERING SPECTROSCOPY

(75) Inventors: Brian D. Hunt, La Crescenta, CA (US); Michael Bronikowski, Altadena, CA (US); Eric W. Wong, Los Angeles, CA (US); Paul von Allmen, Pasadena, CA (US); Fabiano A. Oyafuso, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 230 days.

(21) Appl. No.: 11/512,054

(22) Filed: Aug. 28, 2006

(65) Prior Publication Data

US 2009/0072137 A1    Mar. 19, 2009

Related U.S. Application Data

(60) Provisional application No. 60/713,827, filed on Sep. 2, 2005.

(51) Int. Cl.
*G01N 27/12* (2006.01)
(52) U.S. Cl. ...................................... 250/305
(58) Field of Classification Search .............. 250/305, 250/306, 307
See application file for complete search history.

(56) References Cited

U.S. PATENT DOCUMENTS 4,746,571 A * 5/1988 Kelly .......................... 428/328

FOREIGN PATENT DOCUMENTS

WO    2004/051219 A2    6/2004

OTHER PUBLICATIONS

Appenzeller, et al., "Band-to-Band Tunneling In Carbon Nanotube Field-Effect Transistors", *Physical Review Letters*, vol. 93, 196805 (2004).
Appenzeller, et al., "Comparing Carbon Nanotube Transistors—The Ideal Choice: A Novel Tunneling Device Design", *IEEE Transactions on Electron Devices*, vol. 52, p. 2568-2576 (Dec. 2005).
Chen, J., et al., "Self-aligned Carbon Nanotube Transistors With Charge Transfer Doping", Applied Physics Letters, vol. 86, 123108 (2005).
Chen Z., et al., "An Integrated Logic Circuit Assembled On A Single Carbon Nanotube", *Science*, vol. 311, No. 1735 (Mar. 2006).
Collins, P., et al., Engineering Carbon Nanotubes And Nanotube Circuits Using Electrical Breakdown, *Science*, vol. 292, No. 5517, pp. 706-709 (Apr. 2001).
Kong, J., et al., "Nanotube Molecular Wires As Chemical Sensors", *Science*, vol. 287, No. 5453, pp. 622-625 (Jan. 2000).
Lake R., et al., "Single And Multi-Band Modeling Of Quantum Electron Transport Through Layered Semiconductor Devices", Journal of Applied Physics, vol. 81, No. 12, pp. 7845-7869 (Jun. 1997).

(Continued)

*Primary Examiner*—Kiet T Nguyen
(74) *Attorney, Agent, or Firm*—Steinfl & Bruno

(57) ABSTRACT

Methods and devices for spectroscopic identification of molecules using nanoscale wires are disclosed. According to one of the methods, nanoscale wires are provided, electrons are injected into the nanoscale wire; and inelastic electron scattering is measured via excitation of low-lying vibrational energy levels of molecules bound to the nanoscale wire.

16 Claims, 3 Drawing Sheets

OTHER PUBLICATIONS

Lin, Y., et al., "High-Performance Carbon Nanotube Field-Effect Transistor With Tunable Polarities", *IEEE Transactions On Nanotechnology*, vol. 4, p. 481-489 (Sep. 2005).

Nielson, K.D., et al., "Development Of The ReaxFF Reactive Force Field For Describing Transition Metal Catalyzed Reactions, With Application To The Initial Stages Of The Catalytic Formation Of Carbon Nanotubes", Journal of Physical Chemistry A, vol. 109, No. 3, pp. 493-498 (Nov. 2005).

Wolf, E. L., "Principles Of Electron Tunneling Spectroscopy", Oxford University Press, p. 349 (1985).

Hunt, B., et al., "Carbon and Silicon nanowire chemical sensors for in situ astrobiological measurements" Mars Astrobiology Science and Technology Workshop (Sep. 2004).

Laing, W., et al. "Shell filling and exchange coupling in metallic single-walled carbon nanotubes", Physical Review Letters, vol. 88, No. 12, pp. 126801-1-126801-4 (Mar. 2002).

Matsumoto, K., et al., "Carbon Nanotube SET/FET no Sensor Oyo", Institute of Electrical Workshop, XX, JP, vol. EFM-3, No. 35-44, pp. 47-50 (Dec. 2003).

Stipe, B.C., et al., "A variable-temperature scanning tunnelling microscope capable of single molecule vibrational spectroscopy", Review of Scientific Instruments, vol. 70, No. 1, pp. 137-143 (Jan. 1999).

Yu, L.H., et al., "Inelastic electron tunnelling via molecular vibrations in single-molecule transistors", Physical Review Letters, vol. 93, pp. 266802-1-266802-4 (Dec. 2004).

* cited by examiner

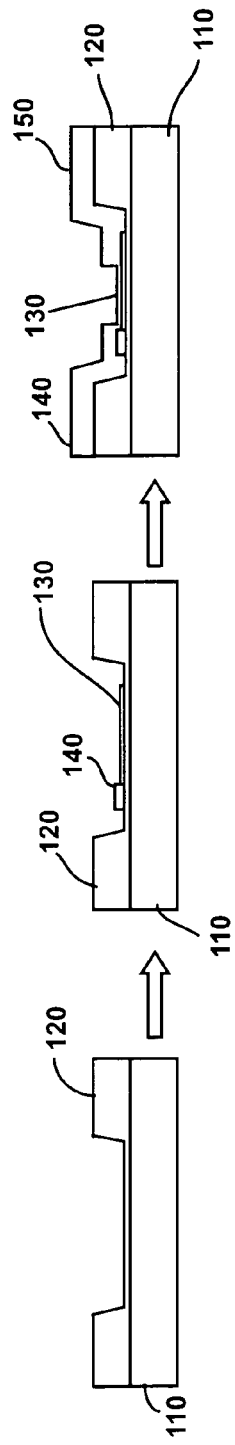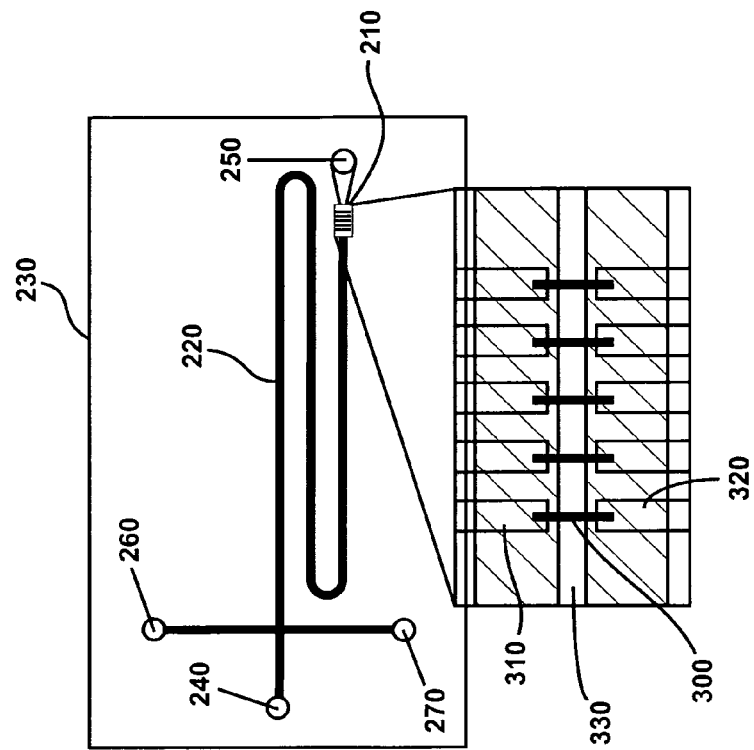

NANOWIRE ELECTRON SCATTERING SPECTROSCOPY

CROSS REFERENCE TO RELATED APPLICATIONS

This application claims the benefit of U.S. provisional Patent Application Ser. No. 60/713,827 filed Sep. 2, 2005 for "Nanowire Electron Scattering Spectroscopy" by Brian D. Hunt, Michael Bronikowski, Eric W. Wong, Paul von Allmen and Fabiano A. Oyafuso, the disclosure of which is incorporated herein by reference.

STATEMENT REGARDING FEDERALLY SPONSORED RESEARCH OR DEVELOPMENT

The invention described herein was made in the performance of work under a NASA contract, and is subject to the provisions of Public Law 96-517 (35 USC 202) in which the Contractor has elected to retain title.

BACKGROUND

1. Field

The present disclosure relates to methods and devices for sensing. In particular, it relates to devices and methods for nanowire electron scattering spectroscopy.

2. Related Art

Optical fluorescence techniques are capable of single molecule sensitivity and are well suited to surveying relatively large volumes. However, optical techniques require labeling with fluorescent "tags", an optical excitation source, and optical detection.

Carbon nanotube (CNT) based chemical sensors offer significant advantages over traditional metal-oxide-based electrical sensors such as chem.-FETs, including very high sensitivity approaching single molecule detection. However, the optimization of such sensors is still in its infancy. It was only very recently that room temperature operation of very sensitive (about 2 ppm) CNT-based chemical sensors was first demonstrated. See Kong J, Franklin N, Zhou C, Chapline M, Peng S, Cho K, Dai H, *Nanotube Molecular Wires as Chemical Sensors*, Science, 287, 622. Such sensors respond to many charged or charge-donating molecules in a similar fashion, and rely on chemical functionalization of the CNT to provide chemical specificity. In particular, chemically functionalized nanowires with preattached chemical receptors tailored to individual molecules of interest must be used.

Therefore, this additional, costly functionalization step must be done differently for each type of molecule and many differently functionalized nanotubes would be required for detection of a broad range of chemicals. As a consequence, while potentially effective, this functionalization requires labor-intensive treatment of many nanowires to sense a broad spectrum of molecules.

SUMMARY

In accordance with the present disclosure, a method for spectroscopic identification of molecules is provided, comprising: providing a nanoscale wire; injecting electrons into the nanoscale wire; and measuring inelastic electron scattering via excitation of low-lying vibrational energy levels of molecules bound to the nanoscale wire.

Low-lying vibrational energy levels are vibrational modes with relatively low excitation energies, less than a few hundred meV.

Also disclosed is a method for fabricating a device for spectroscopic identification of molecules, comprising: fabricating two or more electrodes; growing nanotubes on the electrodes; and providing a source of electrons to be injected into the one or more nanotubes through the two or more electrodes for spectroscopic identification of molecules.

Further disclosed is a method for fabricating a device for spectroscopic identification of molecules, comprising: growing one or more nanotubes; patterning two or more electrodes over the one or more nanotubes; and providing a source of electrons to be injected into the one or more nanotubes through the two or more electrodes for spectroscopic identification of molecules.

Also disclosed is a method for fabricating a device for spectroscopic identification of molecules, comprising: growing one or more nanotubes; patterning at least two electrodes over the one or more nanotubes; patterning a central gate structure between the at least two electrodes; and providing a source of electrons to be injected into the one or more nanotubes through the two or more electrodes for spectroscopic identification of molecules.

Further disclosed is a device for spectroscopic identification of molecules, comprising: a nanoscale wire; two electrodes connected with the nanoscale wire, means for injecting electrons into the nanoscale wire; and means for measuring inelastic electron excitation of vibrational energy levels of molecules bound to the nanoscale wire.

The technique according to the present disclosure is somewhat analogous to an optical technique, Raman spectroscopy, in its ability to measure molecular vibrational levels. Raman spectroscopy is described in more detail in "Analytical Applications of Raman Spectroscopy", Michael Pelletier, Blackwell Publishing, 1999. For both fluorescent and Raman measurements, the optics are typically not integrated on chip, require alignment, and tend to be rather bulky.

In contrast, nanowire sensors do not require lasers or optics and can also operate at single molecule sensitivity, but with simple and direct electrical readout so that sensing and signal processing circuitry can be fully integrated for a compact, ultra-low power system.

The nanowire electron scattering spectroscopy (NESS) technique according to the present disclosure is unique in its ability to detect and identify molecules without the labor-intensive functionalization process. The NESS technique uses derivative measurements of the nanowire current-voltage characteristics to measure conductance (dI/dV) changes of the nanowire as a function of the injected electron energy. Changes in the conductance as a function of voltage bias give a direct readout of molecular vibration energies to enable molecular identification. The NESS readout is more complex than a simple conductance measurement carried out at a single fixed voltage bias, because the technique according to the present disclosure makes use of a bias voltage sweep and conductance measurement as a function of voltage. However, the NESS readout method is still all-electronic, which will enable on-chip integration of the sensor and readout electronics, and eliminate any requirement for bulky and complex optics.

The ability to detect and identify very low-level molecular concentrations in a simple nanowire-based sensor eliminates the need to functionalize large numbers of nanowires. This greatly simplifies the fabrication of sensor systems based on nanowires and provides a robust low power device for identification of molecular species relevant to astrobiology, geochemistry, and astronaut health. Such versatile, reliable and nanoscale sensors could enable entirely new approaches to planetary characterization, for example, by allowing the deployment of large arrays of highly capable chemical sensors.

The concepts used throughout the present disclosure are also somewhat analogous to a technique known as "inelastic electron tunneling spectroscopy" or IETS. See, for example, E. L. Wolf, *Principles of Electron Tunneling Spectroscopy*, p. 349, Oxford University Press, 1985. However, in the IETS approach, the molecules to be analyzed need to be embedded in the tunnel barrier of a tunnel junction during the fabrication of the device. Thus, unlike the NESS concept of the present disclosure, the IETS approach does not allow real-time detection of multiple chemical species presented to the sensor after device fabrication.

BRIEF DESCRIPTION OF THE DRAWINGS

FIGS. 4A-4C show fabrication steps to fabricate the structure according to the present disclosure.

FIG. 6 shows an embodiment where a microfluidic separation column is provided.

DETAILED DESCRIPTION

Figure 1:
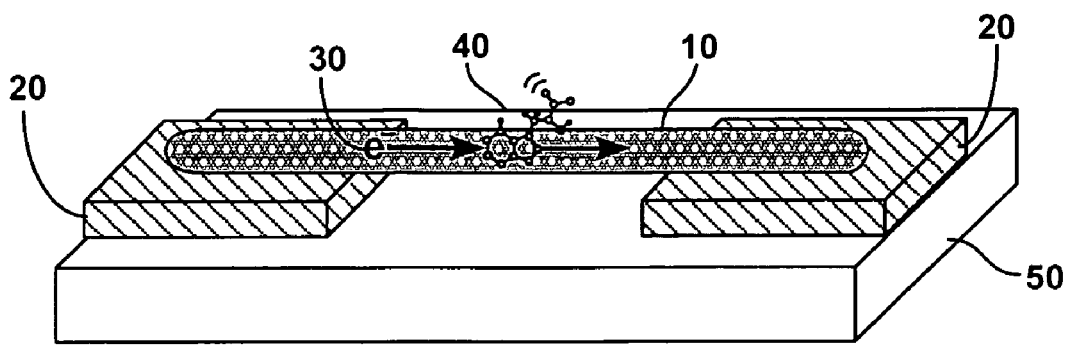
FIG. 1 shows a schematic diagram illustrating the concepts in accordance with the present disclosure.

FIG. 1 is a schematic diagram showing a nanotube or nanoscale wire (nanowire) 10 connected with at least two electrodes 20, thus forming a nanotube suspended bridge. The person skilled in the art will understand that a nanoscale wire has a nanoscale diameter (less than 100 nm), but may have a much longer length on the order of microns or more. The micron scale length enables practical external coupling via electrode contacts in order to monitor the unique electrical properties associated with the nanometer cross-sectional dimensions. Electrons 30 are injected at energies determined by the voltage bias across the nanotube 10. When electron energies correspond to particular molecular vibrational levels in attached molecules 40, enhanced electronic scattering leads to a measurable change in conductance at that voltage. Also shown in the figure is a substrate 50. Typical voltage biases will range from zero to several hundred milli-electron volts (meV) (for example, approximately 0 to 0.30 V), although higher voltage biases up to several volts may also prove useful, depending on the nanowire material. The most likely useful energy range for carbon nanotubes (CNT) is discussed below.

Peaks or dips in the conductance of the nanotube (dI/dV) as a function of voltage bias (electron energy) will give a direct readout of molecular vibrational energies to enable spectroscopic molecular identification.

Inelastic electron excitation of molecular vibrational modes is potentially applicable to identification of many different molecules in a nanoscale ultralow power sensor with a simple readout technique. In particular, as a bias voltage reaches a threshold level for a molecular vibration mode, an additional channel for electron scattering opens up and—under certain conditions—can be observed as a peak in the second derivative curve of the I-V characteristics (i.e. nanotube current—voltage bias characteristics). In this way, spectroscopic identification of the attached molecules is possible in a manner analogous to Raman spectroscopy. The person skilled in the art will understand that the term "inelastic" is a common physics term, which indicates that the energy of the electron changes in the scattering event. In other words, some of the electronic energy is transferred into vibrational modes of the molecule. In contrast, with elastic scattering, there is no change in the electron energy, although the direction of travel may change.

The inventors have noted that a molecule that is chemisorbed or physisorbed (via van der Waals forces) onto the surface of a CNT induces well-defined I-V features associated with the inelastic electron scattering provided that there exist:

1) a narrow-energy-band electron source, 2) a long ballistic mean free path for the injected electrons, 3) efficient coupling between the electrons and the molecule and 4) narrow vibrational bands in the molecule.

Carbon nanotubes (CNT) provide a near-ideal structure for meeting the first three of these requirements. Even at room temperature, the energy bands in nanotubes are relatively narrow due to the singularities in the CNT density of states. Further narrowing of the injected electron energy range can be accomplished using a modified injection technique described below. In carbon nanotubes, low energy (less than about 200 meV) electrons travel ballistically (i.e. without inelastic scattering) over distances on the order of a micron, so that injected electrons will have a nearly uniform kinetic energy for sub-micron length devices. At energies above about 200 meV, the injected electrons can directly excite the C—C bonds in the nanotubes, which provides an internal standard for energy calibration. Working in the energy range of approximately 0 to 200 meV (corresponding to 0.2 V) will allow identification of the vast majority of organic molecules. In regards to the third requirement, since single-walled CNTs are essentially all "surface", electron coupling to molecules on the surface will be maximized.

Finally, the vibrational spectrum of many molecules (e.g., chlorinated hydrocarbons, amino acids, proteins) features narrow bands that will lead to well-defined structures in the I-V (current-voltage) characteristic.

Similarly to other spectroscopic techniques, narrow-band excitation sources should be used to obtain high resolution spectra. Although the thermal energy spread at room temperature is on the order of kT, 25 meV, this spread can be sensibly reduced through the use of appropriate energy filters. See, for example, Appenzeller et al, *Comparing Carbon Nanotube Transistors—The ideal choice: A novel tunneling device design*, IEEE Trans. Elec. Dev. 52, 2568 (December, 2005), incorporated herein by reference in its entirety.

Figure 2A:
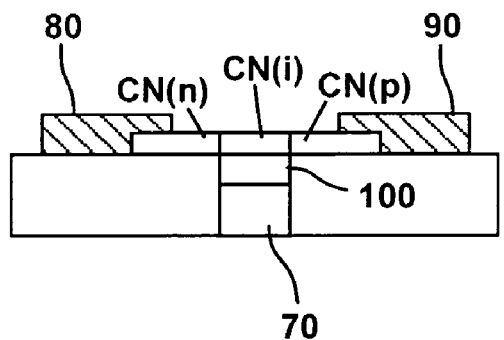
FIGS. 2A and 2B show an embodiment where a narrow-band energy injector is provided.
Figure 2B:
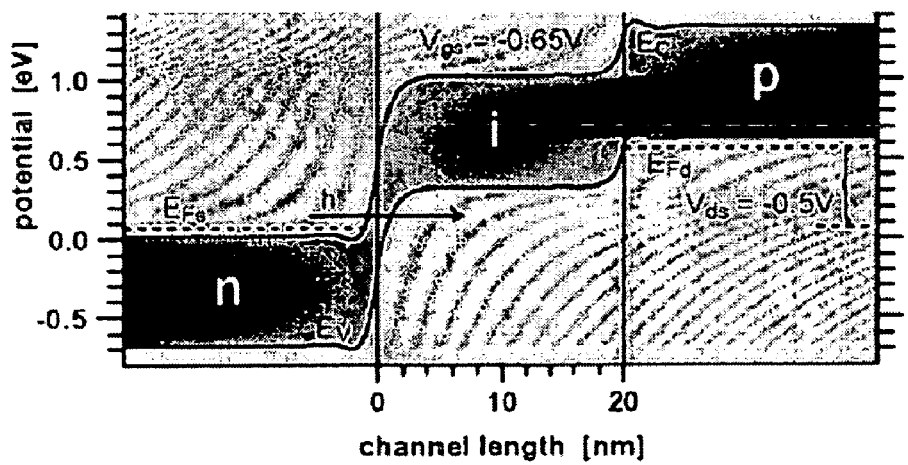

FIGS. 2A and 2B show an embodiment where a narrow-energy-band CNT injector based on the above Appenzeller paper (see also FIGS. 1c and 5 in the above mentioned Appenzeller paper) is used in conjunction with the nanowire electron scattering spectroscopy methods addressed herein. With reference to FIG. 2A, doping is used to establish an n-i-p CNT FET configuration. The gate 70 of the FET is located on the undoped central region CN(i) of the nanotube. Also shown in the Figure are a source region 80 and a drain region 90 of the FET. The source 80 is connected with an n-doped region CN(n) of the nanotube. The drain 90 is connected with a p-doped region CN(p) of the nanotube. An oxide region 100 between the gate 70 and the undoped portion CN(i) is also present.

N-type and P-type doping of the regions CN(n) and CN(p) can be accomplished:

1) electrostatically using one or more additional gates (see also Appenzeller et al, *Band-to-band tunneling in carbon nanotube field-effect transistors*, Phys. Rev. Lett. 93, 196805 (2004), incorporated herein by reference in its entirety) It should be noted that a top gate geometry is also possible, or 2) by chemical doping (see, e.g., J. Chen et al, *Self-aligned carbon nanotube transistors with charge transfer doping*, Appl. Phys. Lett. 86, 123108 (2005), Y. Lin et al, *High-performance carbon nanotube field-effect transistor with tunable polarities*, IEEE Trans. Nano, 4, 481 (2005)), or 3) by appropriate choice of source and drain contact metals (see, e.g., Z. Chen et al, *An integrated logic circuit assembled on a single carbon nanotube*, Science 311, 1735 (2006)).

With reference to FIG. 2B, the gate-source bias voltage Vgs is fixed at a value that closely aligns the n-region conduction band edge with the i-region valence band edge. Due to the gate-induced band bending, the small diameter of the nanotube and the low effective carrier mass in the CNT, the band-to-band (BTB) tunneling current can be quite large (see also Appenzeller et al, Phys. Rev. Lett. 93, 196805 (2004), already cited above).

The key point of the embodiment shown in FIGS. 2A and 2B is that the BTB tunneling from n to i (n-doped region of the CNT to undoped region of the CNT) provides a narrow energy distribution electron source due to the large peak in the density of state (DOS) at the band edges and the cutoff of the high energy tails by the band edges. The n-i injector acts as a bandpass energy filter to give a "cold" narrow electron source injecting into the p region. By sweeping the source-drain bias, Vds, the energy of the electrons injected into the p region can be varied for application to NESS measurements. This approach also works for a symmetrical p-i-p or n-i-n structure, and the effective narrowing of the electron energy distribution has been experimentally verified through measurement of the subthreshold slope in CNT FET transfer characteristics (see Appenzeller et al, *Band-to-band tunneling in carbon nanotube field-effect transistors*, Phys. Rev. Lett. 93, 196805 (2004), also incorporated herein by reference in its entirety).

To enable proper analysis of the data, I-V curves can be simulated using enhancements made to the non-equilibrium Green function (NEGF) transport software developed at Jet Propulsion Laboratory (JPL) under Caltech copyright, which uses a methodology similar to the approach taken in Lake R., Klimeck G., Bowen R. C., Jovanovic D., *Single and Multiband Modeling of Quantum Electron Transport through Layered Semiconductor Devices* J. Appl. Phys. 81, 7845, incorporated herein by reference in its entirety.

JPL NEGF software has recently been extended to model 3D transport through nanowires. The NEGF approach allows for a natural inclusion of the various scattering mechanisms, including carrier scattering off the vibrational modes of the attached molecule. The tight-binding method used within the model employs the atomic-level resolution crucial to the computation of the electronic structure and transport properties, yet its semi-empirical approach enables the modeling of relatively large-scale nanostructures (of the order of hundreds of nanometers).

To compute realistic I-V curves, two additional scattering mechanisms are addressed:

1) carrier scattering off the vibrational modes of the attached molecules. In particular, in order to accurately model the vibrational modes of molecules attached to the CNT, ReaxFF™ software can be used. ReaxFF is a first-principles reactive force fields code developed at Caltech. The results of calculation through ReaxFF can then be used within JPL NEGF software to compute scattering rates off of the vibrational modes. See, e.g., K. D. Nielson, A. C. T. van Duin, J. Oxgaard, W. Q. Deng, and W. A. Goddard III, *Development of the ReaxFF Reactive Force Field for Describing Transition Metal Catalyzed Reactions, with Application to the Initial Stages of the Catalytic Formation of Carbon Nanotubes*, J. Phys. Chem. A 109, 493 (2005).

2) scattering off resonant electronic states associated with the attached molecule. In particular, in addition to the mechanical coupling with the vibrational modes of the adsorbed molecule, there may be significant scattering of carriers off of resonant electronic states associated with the molecule, depending on the strength of the binding of the adsorbate onto the nanotubes. Thus, an electronic (tight-binding) characterization of the molecule is also preferred for such cases. Once the coupling of the molecule is characterized, however, carrier scattering is handled automatically within the RGF formalism of JPL NEGF software.

Derivative measurements of the current-voltage characteristics provide a direct indication of electron scattering as a function of electron injection energy, which is set by the voltage bias across the nanowire. Such measurements are analogous to inelastic tunneling spectroscopy (IETS) performed with molecular-doped tunnel junctions.

Figure 3:
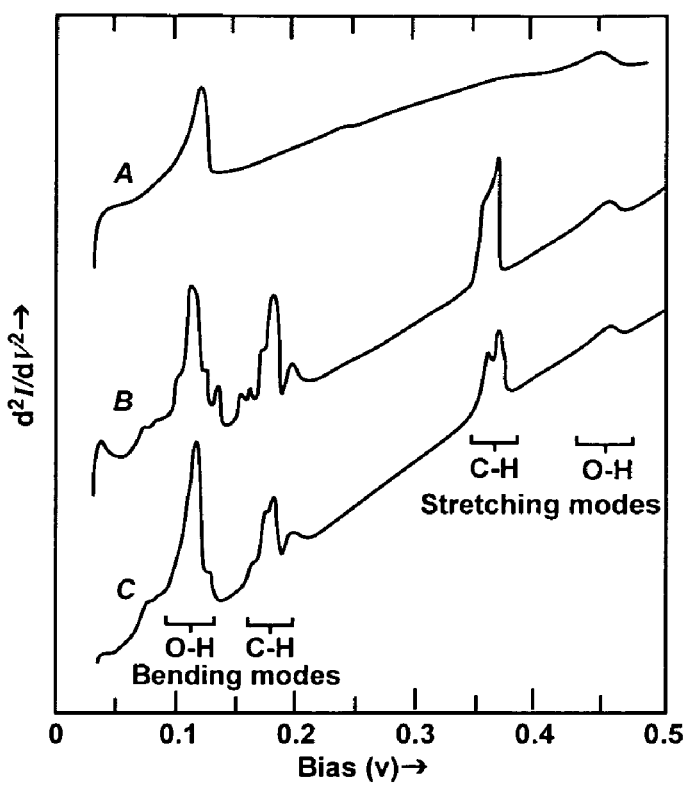
FIG. 3 shows vibrational spectra for Inelastic Electron Tunneling Spectroscopy (IETS) for a Al—$Al_2O_3$ Pb junction, taken from E. L. Wolf, *Principles of Electron Tunneling Spectroscopy*, p. 349, Oxford University Press, 1985.

FIG. 3 shows a classic IETS spectrum measured with a doped two-dimensional tunnel junction, as an example of the type of data expected from this effort.

The 1-D nanowires allow much more efficient coupling to molecules than the tunnel junctions to give far greater sensitivity. Also in contrast to the tunnel junctions, the nanowire geometry exposes the active sensing area, the outside of the nanowire, to enable real-time measurements of changing molecular concentrations. With the tunnel junctions, the molecules under study are embedded in a solid-state device during fabrication, so new devices must be produced for each molecule to be examined.

Molecule-nanotube interactions and molecular structure determine electron scattering from the molecule. Theoretical simulations can help establish how the multitude of vibrational modes will have different scattering cross sections, thus providing a set of selection rules analogous to Raman spectroscopy. A library of NESS spectra or fingerprints can be built through experiments. Simulations can aid interpretation of the spectra and can help predicting what types of molecular structure are best suited for NESS.

Fabrication of devices comprising nanotubes suspended across electrodes will now be discussed. This can be done by first fabricating the electrodes and then using chemical vapor deposition (CVD) to grow nanotubes from a predefined catalyst region on one or both electrodes. However, since the nanotubes rest on top of the electrodes, there is significant contact resistance between the electrode and the nanotube (typically about 100-500 kOhm). To enable efficient electron injection into the nanotubes, fabrication techniques can be developed to minimize such contact resistance by using, for example, CNT-Pd—Au, CNT-Ti—Au, CNT-Ti—Pd, or CNT-Ti—Pd—Au ohmic contacts. Also ohmic contacts comprised of Pt alloys can be used.

This can be done by reversing the processing order, as illustrated in FIGS. 4A-4C, where a silicon substrate 110 and a SiO$_2$ region 120 (suitable for forming, among others, regions such as region 100 of FIG. 2A) are shown. In particular, nanotubes 130 will first be grown from predefined catalyst regions 140 and then electrodes 140, 150 will be patterned over the nanotubes 130. As shown in FIG. 4A, oxide windows are patterned and thin oxide is regrown. With reference to FIG. 4B, a catalyst 140 is lifted off and a nanowire 130 is grown. In FIG. 4C, electrodes 140, 150 are lifted off (e.g. Ti/Au electrodes) with an optional SiO cap (not shown in the Figure). If an additional gate is desired (in addition to the gate provided by the Si wafer 110), as illustrated by element 70 in FIG. 2A, a central Al/Al$_2$O$_3$ top gate structure can be added to the device. The person skilled in the art will understand that the fabrication method of FIGS. 4A-4C can be performed in more or less steps than those shown in the Figures.

Submicron CNT suspended bridges will be produced to minimize the effects of acoustic phonon scattering within the nanotubes. Because the ballistic mean free path in CNTs is approximately one micron, submicron nanotube lengths will allow most of the injected electrons to travel along the tube without scattering (except off of adsorbed molecules, as desired). Because approximately ⅓ of the nanotubes grown by CVD are metallic and ⅔ are semiconducting, in some cases it may be desirable to selectively destroy the metallic tubes, for example if the narrow band energy injection scheme shown in FIG. 2A is used. In these cases, the metallic CNTs can be selectively burned off using procedures known to the person skilled in the art (see, e.g., P. Collins, M. Arnold, P. Avouris, *Engineering Carbon Nanotubes and Nanotube Circuits Using Electrical Breakdown*, Science 292, 706 (2001), also incorporated herein by reference in its entirety). For example, this can be done by gating the nanotubes to shut off current in the semiconducting CNTs, thereby shunting all current through the metallic nanotubes.

Figure 5:
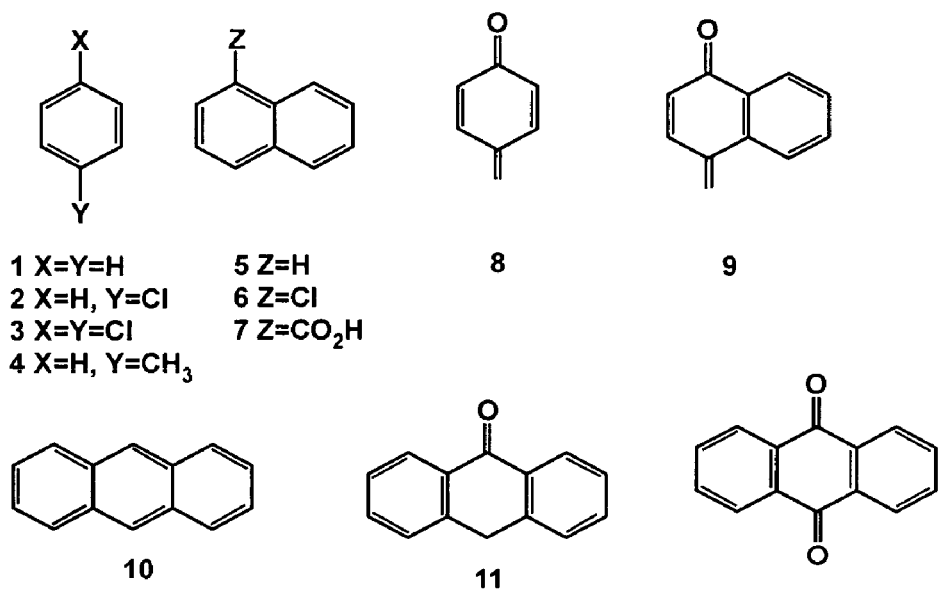
FIG. 5 shows examples of molecules suitable for experimental and theoretical NESS studies.

To demonstrate NESS, nanotube devices can be exposed to controlled doses of analytes, as shown in FIG. 5, in gaseous and liquid forms. Derivative techniques (e.g. using numerical methods or a lock-in amplifier) can be used to analyze features in the current-voltage characteristics associated with inelastic electronic excitation of molecular vibrational levels. Using the current generation of nanotube bridges, derivative spectroscopy can be performed on simple benzene derivatives such as molecules 1-4 and 8 in FIG. 5. In general, however, the NESS technique should be applicable to a broad range of molecules including amino acids and proteins, among others.

Because of variable contact resistances, some spectra may have undesirable noise and variation. Improved spectral data will be obtainable after development of low contact resistance nanotube devices as described above. To obtain low noise measurements, the devices can be packaged so as to allow delivery of gaseous and liquid analytes while also maintaining good electrical shielding.

In order to simplify the interpretation of complex spectra expected with mixtures of chemicals, the nanotube sensors can be integrated with a microfluidic separation column, such as a capillary electrophoresis (CE) column. Incorporation of such a column enables separation and concentration of chemical species, which would then be sensed and identified at the outlet using the NESS technique.

FIG. 6 shows a top view of such embodiment, where a plurality of nanowire sensors 210 is provided in a microfluidic separation column 220 of a CE chip 230. Also shown in the figure are the anode region 240, the cathode (ground) region 250, the sample injection inlet 260 and the waste outlet 270 of the column. The enlargement of element 210 shows the arrangement of the nanowire sensors 300, bridging respective pluralities of electrodes 310, 320 and forming a fluidic channel 330. This embodiment enables analysis of complex solutions. Pre-separation of the various solution components simplifies the nanowire spectroscopic analysis because the nanowires are exposed to only one molecular species at a time.

Following initial experimentations, the device geometries will be re-optimized based on the above experimental and theoretical results. For instance, the length of the nanotube bridge may have to be shortened to increase the number of ballistic electrons. After optimizing the devices, NESS can be obtained for more complex polycyclic aromatic hydrocarbons (PAHs) such as the naphtalene derivatives (5-7 and 9) and anthracene derivatives (10-12) shown in FIG. 5 for comparison to theoretical results. Finally, molecules can also be tested using low temperature measurements to further narrow the injected electron energy spread. In conjunction with simulations, this can allow better understanding of the scattering mechanisms and the general applicability of NESS to other molecules.

Nanowires of other materials such as Si may also yield usable NESS signals. While the signals from such nanowires are expected to be smaller than those for CNT-based sensors, the surface chemistry of these wires could allow detection of chemical species that do not readily bind to nanotubes.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

What is claimed is:

1. A method for spectroscopic identification of molecules, comprising:
    providing a nanoscale wire;
    injecting electrons into the nanoscale wire; and
    measuring inelastic electron scattering via excitation of low-lying vibrational energy levels of molecules bound to the nanoscale wire.

2. The method of claim 1, wherein the nanoscale wire is a carbon nanotube nanoscale wire.

3. The method of claim 1, wherein the nanoscale wire is a silicon nanoscale wire.

4. The method of claim 1, wherein injecting electrons is performed by providing the nanoscale wire with a voltage bias and measuring is performed by detecting behavior of conductance in the nanoscale wire as a function of the voltage bias.

5. The method of claim 4, wherein detecting behavior of conductance in the nanoscale wires is performed by identifying peaks and dips in the conductance waveform.

6. The method of claim 4, wherein detecting behavior of conductance in the nanoscale wire as a function of the voltage bias leads to identification of molecular species through a non-equilibrium Green function (NEGF) analysis software.

7. A device for spectroscopic identification of molecules, comprising:
    a nanoscale wire;
    two electrodes connected with the nanoscale wire,
    means for injecting electrons into the nanoscale wire; and
    means for measuring inelastic electron excitation of vibrational energy levels of molecules bound to the nanoscale wire.

8. The device of claim 7, wherein said vibrational energy levels have an energy of less than 300 meV.

9. The device of claim 7, wherein the nanoscale wire has a first region connected with a first electrode of the two electrodes and a second region connected with a second electrode of the two electrodes.

10. The device of claim 9 wherein the first region and the second region are doped, doping of the first region and the second region being respectively selected from one of the following combinations: n-doping and n-doping; p-doping and p-doping; n-doping and p-doping; p-doping and n-doping.

11. The device of claim 9, wherein the nanoscale wire has a third region located between the first region and the second region.

12. The device of claim 11, wherein the third region is an undoped region.

13. The device of claim 12, wherein the first region is connected with a source of a FET transistor, the second region is connected with a drain of the FET transistor.

14. The device of claim 13, wherein the third region is connected to a gate of the FET transistor through an oxide layer.

15. An arrangement for capillary electrophoresis, comprising the device of claim 7.

16. The arrangement for capillary electrophoresis of claim 15, further comprising a microfluidic separation column, the microfluidic separation column comprising said device.

* * * * *